United States Patent [19]

Johnson et al.

[11] Patent Number: 5,215,662
[45] Date of Patent: Jun. 1, 1993

[54] HEAT RESISTANT MICROPOROUS MATERIAL PRODUCTION AND PRODUCTS

[75] Inventors: James S. Johnson, Acton; Edward T. Carter, Worcester, both of Mass.

[73] Assignee: Micron Separations Inc., Westborough, Mass.

[21] Appl. No.: 583,387

[22] Filed: Sep. 17, 1990

Related U.S. Application Data

[63] Continuation-in-part of Ser. No. 285,787, Dec. 16, 1988, abandoned.

[51] Int. Cl.⁵ .............................................. B01D 71/56
[52] U.S. Cl. ................... 210/500.38; 55/158; 264/45.1
[58] Field of Search ............. 264/45.5, 41, 45; 210/500.38, 500.37; 55/158

[56] References Cited

U.S. PATENT DOCUMENTS

| | | |
|---|---|---|
| 3,408,315 | 5/1973 | Paine . |
| 3,876,738 | 4/1975 | Marinaccio et al. . |
| 4,340,480 | 7/1982 | Pall et al. ........................ 264/41 X |
| 4,408,036 | 10/1983 | Gaymans et al. . |
| 4,431,545 | 2/1984 | Pall et al. . |
| 4,446,304 | 5/1984 | Gaymans et al. . |
| 4,450,126 | 5/1984 | Kesting . |
| 4,460,762 | 7/1984 | Gaymans et al. . |
| 4,617,235 | 10/1986 | Shinohome et al. ................. 428/374 |
| 4,693,985 | 9/1987 | Degen et al. . |
| 4,716,214 | 12/1987 | Gaymans et al. . |
| 4,719,284 | 1/1988 | Nielinger et al. . |
| 4,722,997 | 2/1988 | Roerdink et al. . |
| 4,774,038 | 9/1988 | Ditter et al. ........................... 55/158 |
| 4,788,226 | 11/1988 | Curry ............................. 210/500.38 |
| 4,814,356 | 3/1989 | Bongers et al. .................. 525/420 R |
| 4,921,654 | 5/1990 | Hov et al. ........................... 264/45.5 |

FOREIGN PATENT DOCUMENTS

WO8607544 12/1986 PCT Int'l Appl. .

*Primary Examiner*—Frank Sever
*Attorney, Agent, or Firm*—Bruce F. Jacobs

[57] ABSTRACT

Microporous nylon materials which retain near constant time to hydrosaturation during and after heating to temperatures necessary for sealing together a plurality of surfaces, and the synthesis thereof. Nylon 46 dissolved into a mixture of liquid nylon 46 solvents and nonsolvents is dispersed on a fabric substrate, then precipitated to form a laminate, from which a wash removes the nonsolvents and forms the microporous material.

25 Claims, 4 Drawing Sheets

HEAT RESISTANT MICROPOROUS MATERIAL PRODUCTION AND PRODUCTS

This application is a continuation-in-part application of Ser. No. 07/285,787, filed Dec. 16, 1988, now abandoned.

FIELD OF THE INVENTION

This invention relates generally to heat resistant microporous materials produced from a polyamide resin which is suitable for use in such applications as filtering bacteria from solutions, binding DNA in hybridization research and chromatography.

BACKGROUND OF THE INVENTION

Microporous materials have varied applications in the fields of separations, analytics and absorption. Filtration is the most fully developed of these arts and provides some technical background for the instant invention.

Microporous materials are characterized by their filtrate permeability (flow rate), minimum particulate retention size (pore size), continued permeability as particulates are collected, (clogging resistance), strength, dimensional stability, and wettability.

The flow rate of a porous material is a measurement of volume of fluid passage per unit time for a given depth and area of the material at a known differential pressure. Flow rate is influenced by the size, internal physical structure and distribution of the pores; for a given material area, depth and maximum pore size (measured by bubble point or particulate challenge), lower flow rates indicate fewer pores, a greater portion of smaller sized pores, or both.

Pore size may be characterized by the bubble point,[1] a measurement of the gas pressure required to remove a liquid from the pores of a saturated material. Bubble point measurements are typically reported for the removal of water by air, a standard of comparison now recognized in the microfiltration industry. If, for example, a filter formed from microporous material exhibits a bubble point of 6 psi and a flow rate of 13 cc/min cm$^2$ at 10 psi, then the relationship of flow rate and bubble point is not good relative to commercial filters. This bubble point is indicative of a pore size of around 5.0 um, whereas the flow rate is indicative of a 0.2 um pore size. This condition produces a membrane of poor filtration performance, having a comparatively low flow rate for the maximum pore size of 5 um.

[1] American Society for Testing and Materials, Standard F316; and Brock, Thomas D., Membrane Filtration: A User's Guide and Reference Manual, Science Tech, Inc., Madison, Wis., 1983.

Pore size can also be measured by particulate challenge, the process of checking a material's particulate retention for progressively smaller particulates of known dimensions. Gradients of particulate size are commercially available and detection of particulate passage through the material is possible by a variety of analytical techniques, such as light scattering analysis, turbidity analysis, or subsequent smaller pore filtration and particle counts. Particulate challenge is generally more accurate and convenient for pore sizes greater than 50 um than are bubble point determinations.

Clogging resistance is measured by passage or absorption of successive aliquots of a solution containing particulates retained by the material, then comparing the passage or absorption time of the successive aliquots. Commercial scale filtration of microscopic particulates has long been complicated by filters formed from materials which rapidly clog, and thus require frequent cleaning or replacement, thereby limiting filtration capacity.

Strength and dimensional stability of porous materials determine the manufacturing tolerances required for successful formation of commercial grade products, the differential pressure which the materials can withstand, as well as resistance to mechanical tear. For example, in filtration applications swelling and growth of unsupported nylon materials due to solvent absorption can cause mechanical problems.

Wettability is a material's propensity to absorb a particular solvent, and can be measured by the weight percentage of solvent absorbed at saturation, or by the time required for dry materials to reach saturation upon direct contact with the solvent ("wet out time"). Because some porous nylon materials are reported to exhibit reduced wettability at or near their melting points. See Pall, U.S. Pat. No. 4,340,479, saturation capacity and saturation time are generally considered as specific to temperature ranges. While the performance of porous materials with low wettability can be improved by pre-wetting with low surface tension solvents, followed by flushing with the target solvent immediately prior to use, pre-wetting is not only expensive due to cost of the additional solvent, but also due to the additional steps required to use the material for its intended purpose.

Because porous materials are often formed in sheets, fabrication of commercial products often requires sealing multiple surfaces of the material in order to form desirable configurations, for example, filtration cartridges. Seals formed by heating and then placing in contact the affected surfaces are inexpensive and do not require the use of adhesives which might contaminate the filtrate. Thermally formed seals however often reduce the wettability of porous nylon materials.

Several filters have been synthesized from nylon polymer materials. Paine's U.S. Pat. No. 3,408,315 describes a membrane made by first dissolving nylon polymer in a solvent or solvents, forming a base solution and then adding other miscible reagent mixtures to the base solution. A thickening agent such as Cab-O-Sil fumed silica is added to increase the viscosity of the solution to the range of 500–1000 centipiose (Brookfield). Paine's nylon terpolymer solution is then metered onto a belt and the solvents are evaporated, causing precipitation of the nylon into a thin film porous structure. This is known as an air casting process because air is used as the fluid to carry away the solvents from the film of polymer solution.

Paine membranes have limited utility due to their solubility in alcohol and many other solvents. Film membranes produced by this casting method have relatively weak tear and puncture resistance and undergo problematic dimensional changes when wetted with water or on drying after being wet with water.

Marinaccio et al.'s U.S. Pat. No. 3,876,738 describes a process for producing alcohol insoluble microporous membranes of nylon polymers using a wet casting process in which a liquid in contact with the cast film serves to remove the solvent from the polymer containing solution. The Marinaccio process involves metering a controlled thickness of polymer solution onto a drum which is partially longitudinally immersed in a bath containing a non-solvent for the polymer. As the drum rotates the cast film is immersed into the bath. As the solvent is extracted by the bath, the polymer precipitates as a film on the drum; removal of the film and subsequent processing are determined by the intended end use of the film.

Pore formation in Marinaccio's method is dependent upon polymer concentration, the solvent system used to make the polymer solution, the age of the polymer solution, composition of the solvent extraction bath, bath temperature and additives to the mix or the bath. Marinaccio explains that the pore size would increase slightly with polymer concentration because of the increasing aggregation tendency at higher concentrations because the more polymer in solution, the longer the chains of these polymers, and hence the larger spherical shape they will form when precipitated. These aggregates are Marinaccio's means of controlling pore sizes and these aggregation tendencies are modified by using various ratios of non-solvent to solvent, thereby changing the overall solvent power of the solution.

Marinaccio's film membranes suffer from relatively low tear resistance and strength, and dimensional instability. Because nylon polymers readily absorb up to eight weight percent water, the films swell and grow in size, causing problems in filtration and other uses.

Pall's U.S. Pat. No. 4,340,479 claims a skinless, microporous, hydrophilic polyamide membrane produced from alcohol insoluble, hydrophobic nylon polymers, a phenomenon which he claims only occurs with ". . . ratios of $CH_2$ (methylene) to NHCO (amide) within the range from about 5:1 to 7:1." (Column 8, line 24), thus teaching away from the use of polyamide polymers with a $CH_2$ to NHCO ratio outside the range of 5:1 to 7:1 when synthesizing hydrophilic membranes.

Pall's method begins with nylon 66 resin dissolved in a solvent by a mixing regimen. To this starting solution another solution or non-solvent blend is added to create a visible precipitate of polymer, a necessary stage which results in what Pall terms "nucleation" or a "state of nucleation". The precipitate is then totally or partially redissolved to form a casting solution which is formed into a thin film on a substrate and with minimum delay is immersed in a bath which is comprised of a nonsolvent for the polymer and a solvent for the starting solvent. Pall states that many factors influence the nucleation state of the casting solution and hence the final filter properties. These include the temperature of the starting polymer and solvent; the rate and intensity of mixing by which the non-solvent mixture is added; and, the geometry of the mixing vessel.

Pall describes alcohol-insoluble polyamide resins as inherently "hydrophobic," and claims a method of producing from these resins membranes which are "hydrophilic" unless heated to near melting where they revert to the "hydrophobic" state. Because the near melting point temperatures used to effect thermal seals can result in a reversion of these membranes to a "hydrophobic" state, Pall membranes may not be wettable in the seal area with high surface tension solvents such as water and therefore difficult to test and problematical in application.

OBJECT AND SUMMARY OF THE INVENTION

The instant invention is a microporous material with pore sizes which range from about 0.01 um to about 100 um which retains its wettability over a range of temperatures sufficient to form thermal seals between adjacent portions of the material, and the process for synthesizing such materials. These seals are formed by a variety of mechanisms, which functionally define the particular temperatures at which the wettability of the material will not substantially degenerate over the period of time required to form a seal.

These porous materials are produced from nylon 46, a polyamide only recently made available commercially in the United States, synthesized by a polymerizing condensation reaction using diaminobutane and adipic acid as feed stocks. Nylon 46 is alcohol insoluble and has a $CH_2$ (methylene) to NHCO (amide) ratio of 4:1.

Relative to porous materials, and particularly in comparison to commercially available nylon filtration membranes, porous nylon 46 materials of this invention exhibit surprising clogging resistance and chemical resistance to a broad range of solvents and solutes. Users of filters and other devices incorporating porous nylon 46 materials of this invention, such as pleated filter cartridge elements in a filtration system, will realize increased throughput rates, longer cartridge life and more fluid filtered per cartridge with reduced down time to replace dirty, clogged filter elements, and an obvious cost reduction.

The wettability of nylon 46 microporous materials is substantially increased compared to other nylon products as demonstrated by the water absorption of nylon 46 as compared to nylon 66. At saturation nylon 46 absorbs 12 weight percent water (Allied Signal Product Bulletin 1987) whereas nylon 66 absorbs 8.5 weight percent. (DuPont Zytel Product Bulletin E 09134 Aug. 1978). This 40 percent increase in water absorption shows that nylon 46 has a higher affinity for water, hence is more wettable. In contrast with other nylon materials, the superior wettability of nylon 46 membranes enables direct contact saturation with solvents having higher surface tensions than water without using alcohol or some other fluid of low surface tension to prewet the material, thereby avoiding contamination by prewetting fluid and the resulting waste material produced when the wetting fluid is flushed from the material.

Another advantage of nylon 46 is increased temperature resistance resulting from the polymer's melting point of 290° C. compared to 255° C. for nylon 66.

The instant invention entails a microporous material and process parameters used to produce this material. The nylon 46 polymer is dissolved in a mixture of solvents and nonsolvents at a temperature and with sufficient agitation to completely dissolve the polymer without substantial polymer degradation. Solid materials are formed in a bath by precipitating the polymer solution in a controlled manner to produce a uniform pore structure. The precipitation bath is followed by a rinse tank which removes residual solvent from the material.

DETAILED DESCRIPTION OF THE INVENTION

Figure 1:
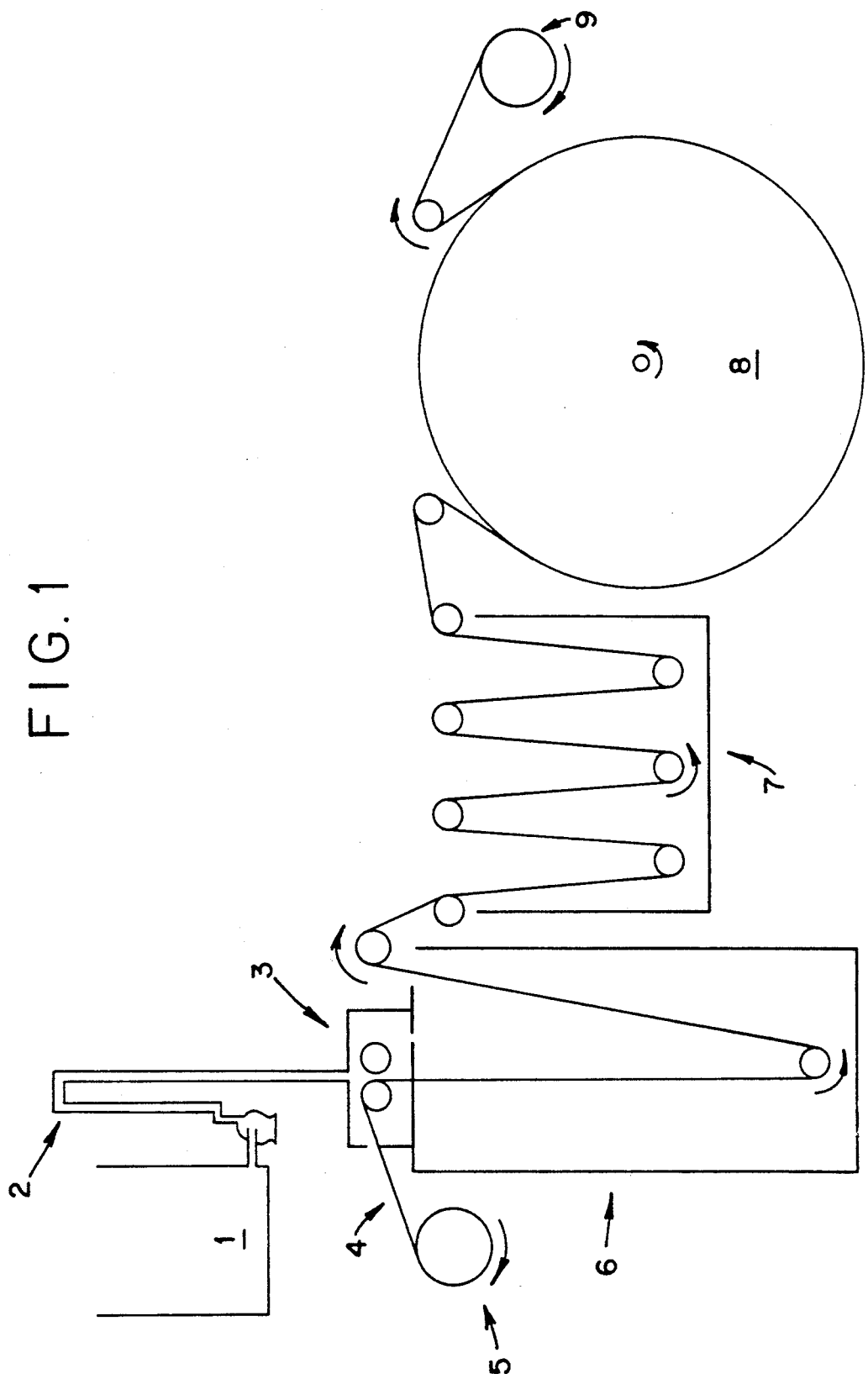
FIG. 1 represents a preferred embodiment of the process for producing sheets of microporous, hydrophilic filter from nylon 46 in accordance with the present invention employs a knife-film forming mechanism.

This invention uses nylon 46, a commercially new polyamide resin, to form a microporous, heat resistant, material with pore sizes ranging from about 0.1 um to about 20 um. In a container the solvents and nonsolvents for the nylon 46 are blended, then nylon 46 is mixed into the liquid until dissolved. The solvents are chosen from the group of aqueous bronsted acids, including but not limited to, hydrochloric acid, formic acid, phosphoric acid, and mixtures thereof. The nonsolvents are chosen from the group comprised of polar organic liquids which when mixed with the polymer and solvent result in the desired pore size of the filter, including but not limited to, methanol, ethanol, propanol, aqueous citric acid, water and mixtures thereof, with the preferred nonsolvent being water. Because greater proportions of nylon 46 polymer in the mix produce smaller pores in the resulting filter, a range of pore sizes from about 0.1 um to about 20 um can be produced from the range of about 11-16 weight percent nylon 46 polymer added to a mix of about 40-50 weight percent standard commercial reagent concentration ("reagent concentration") solvent and about 34-49 weight percent reagent concentration nonsolvent.

Nylon 46 is slowly added into the mixing solvents and nonsolvents at temperature range of about 25°-80° C. at a speed sufficient to prevent the polymer from clumping, but insufficient to cause overheating and polymer degradation. Within this range, higher temperatures cause dissolution to proceed more rapidly and the mix time to total dissolution can be decreased.

A variety of mixing devices for blending pellitized or powered solids with liquids to form viscous fluids are known in the art. The mix times necessary to dissolve the polymer range up to about 6 hours, depending upon the condition of the polymer; a finely powdered polymer will dissolve more quickly than an extruded, pelletized polymer.

After mixing is completed and the polymer is dissolved, the mix is filtered to remove any extraneous particles which would present problems in lacquer delivery or occlusions in the membrane.

Air bubbles created in the mixing step are then eliminated, preferably by letting the solution stand, thus preventing voids or defects in the material.

The solution is then cast into the shape of the desired material. Filter membranes are cast by dispersion into a uniformly thick film, preferentially upon a nonwoven web material. As previously noted, the relative proportions of nylon 46 and nylon 46 solvents and nonsolvents determine in part the pore size and density of the resulting material.

Since higher solution temperatures result in somewhat larger pore sizes, temperature controls can be further used to manipulate the pore size of the material. The dispersion system can include temperature controls, preferentially a heat exchanger, to change the viscosity of the mixture as is necessary to obtain a smooth, even coating of the mixture. As the temperature of the mixture rises, and as these higher temperatures are maintained for longer periods of time, pore size is increased. This feature allows production flexibility because the solution's temperature can be manipulated to produce a range of pore sizes from a single batch of solution. The composition and process temperature control manipulations enable continuous production of the material with fixed or variable pore size and distribution from a single batch of nylon 46 solution.

A solution of nylon 46 lacquer (1) is pumped through a system of piping containing a heat exchanger (2) to the coating mechanism (3). The lacquer is dispersed on a supporting surface, preferably a nonwoven cloth web (4) to form a uniformly thick composite, preferably by drawing the cloth web through a knife box within coating mechanism (3) which controls the thickness of the coating to the desired setting. The lacquer coated web then travels through an acid quench bath (6) causing precipitation of the polymer. The precipitated polymer coated web is then passed through a rinse tank (7) to remove residual solvents. A dryer (8) reduces the moisture content of the precipitated polymer coated web, resulting in the production of the microporous material. A wind up device (9) is used to roll the sheet of material onto a core for convenient storage.

The preferred dispersion system, a coating mechanism (3), is used to create a film of the solution, preferentially supported by a nonwoven fabric substrate. In the preferred embodiment a uniformly thick film of the mixture is assured by the knife box having an adjustable gap which allows the final thickness of the membrane to be controlled. The cast mixture is then exposed to a bath comprised of both solvents and nonsolvents for nylon 46 in a range of compositions such that microporous nylon 46 polymer is precipitated in a uniform, consistent manner. Since smaller pore size materials result from higher proportions of solvents in the bath, a range of different pore sizes can be produced from a single batch of solution. The bath composition can range from about 0-60 weight percent hydrochloric, formic, citric or phosphoric acids, the percentage of stronger acids being chosen from the lower portion of this range. The remaining weight percentage is comprised of one or more of the previously recited nonsolvents. The bath concentrations are varied along with the lacquer composition to produce the desired material pore size.

The extreme hydrophilic nature of nylon 46 causes it to swell as much as 25 percent on wetting or shrink a similar amount on drying a water-wet membrane.

The web-supported nylon 46 membranes of the present invention do not undergo any substantial dimensional changes on wetting or drying common in unsupported membranes (which can be as high as 25 percent). The effect of dimensional changes can be devastating when unsupported membranes are utilized. For example, one cannot precut the disks or other membrane shapes to size since they will almost certainly not retain those dimensions due to changes in humidity or due to prewetting these membranes.

Alternately, a filter plug for columnar applications can be cast from a cylindrical or other three dimensional mold, then exposed to the bath.

The nonsolvents are then extracted from the precipitated nylon 46 by a substance with higher affinity for the nonsolvents than nylon 46, preferably by passage through a rinse tank (7) utilizing a series of rollers to lead the membrane to contact with water in a tortuous path. Extractables are materials which can leach out of the material when in contact with a fluid, and could lead to contamination of process fluids. The nylon 46 material produced by this invention is low in extractables, typically less than 0.1 percent by weight.

Excess moisture is removed from the filter, ideally by a hot air dryer (8) positioned to blow across the material when supported by a rotating drum. Filtered air heated with resistance heaters to a temperature in the range of 80°-200° C. can be used. The dry material is then rolled up on a core (9) for storage and subsequent use.

The nylon 46 polymers used herein may be of a wide range of molecular weights. Examples of suitable nylon 46 polymers include KS200, KS300, and KS400, all commercially available from DSM Corporation, Holland.

The porous materials produced according to this invention have a uniquely bimodal pore structure. More particularly, scanning election micrographs of the porous material produced according to the present invention show the interior of the material to have large interconnecting pores or chambers that do not appear at the surface of the material.

This property of the materials produced according to the present invention can be further characterized by measuring the relative sizes of the pores in the surface and in the interior of the membrane. It has been found that the interior pores of the material are from about two to about ten times the diameter of the largest pores in the membrane surfaces. In addition, it has been found that membranes produced from the materials of the present invention have a porosity greater than about 50 percent.

In contrast, the microporous nylon 66 membrane described in Pall is "skinless", i.e. the membrane are said to have pores extending from surface to surface that are substantially uniform in shape and size. Likewise, the microporous membrane described in U.S. Pat. No. 4,788,226 (Curry), which is said to be formed either of polytetramethylene adipamide alone or in admixture with at least one other polyamide, is also said to be skinless.

It has been found that at least in the range of 75 to 150 microns in thickness, the membranes of the present invention improve with increasing thickness, i.e., by increasing the thickness, the apparent pore size decreases without significant effect on the water flow rate.

Heat resistant microporous materials produced according to this invention can be fashioned into desirable configurations and products by thermal seals which do not impair the wettability of the material. The wettability of this material is not substantially impaired after seals are formed at temperatures maintained for periods of time necessary for the sealing mechanisms of thermoplasticity, fusion, welding, glass transitions, solid/liquid phase transformation, softening point or when steam sterilized or exposed to temperatures of 126°-135° C. for about 45 minutes.

These materials are useful for filtration of bacteria from solutions, for separations required in biotechnical processes and for certain medical procedures, for absorption of contaminates and for separation techniques such as chromotography.

EXAMPLE 1

Unsupported Material

A solution of 14 weight percent nylon 46 polymer (KS200, commercially from available DSM Corporation), 5.45 weight percent hydrochloric acid, 40.5 weight percent citric acid and 40.05 weight percent water was mixed at 30 degrees centigrade for 5 hours. The mix was cast onto a glass plate then immersed into a bath containing 29 weight percent citric acid and 71 weight percent water. The film produced was rinsed with water and removed from the glass plate. The material's mean clean water flow rate was 28 cc/min cm$^2$ at 27" mercury differential pressure with a bubble point of 24 psi, indicating a pore size of about 0.5 um, at a thickness of 110 um.

EXAMPLE 2

Large Pore Size Supported Material

A solution of 12 weight percent nylon 46 polymer (KS200), 5.7 weight percent hydrochloric acid, 41.2 weight percent citric acid and 41.1 weight percent water was mixed at 35 degrees centigrade at a mixer speed of 1300 rpm for 4 hours. This solution was cast onto a non-woven polyester substrate in a bath of approximately 25 weight percent citric acid, 1 weight percent hydrochloric acid and 74 weight percent water. The mix produced a sheet of material 70-80 um in thickness with a mean clean water flow rate of 90cc/min cm$^2$ at 27" mercury differential pressure and a bubble point of 12 to 15 psi, a pore size of approximately 0.8 um.

Example 3

Small Pore Size Supported Material

A solution of 14 weight percent nylon 46 polymer (KS200), 5.7 weight percent hydrochloric acid, 40.5 weight percent citric acid and 39.8 weight percent water was mixed at 35 degrees centigrade at a mixer speed of 1300 rpm for 4 hours. This solution was cast onto a non-woven polyester substrate then passed through a bath of approximately 30 weight percent citric acid, 2-3 weight percent hydrochloric acid and 67-68 weight percent water. This solution produced a filter of 70-80 um in thickness with a mean clean water flow rate of 5.5cc/min cm$^2$ at 27" mercury differential pressure and a bubble point of 75-85 psi, a pore size of approximately 0.1 um.

EXAMPLE 4

Variable Pore size Supported Material

A solution of 14 weight percent nylon 46 polymer (KS200), 5.4 weight percent hydrochloric acid, 40.5 weight percent citric acid and 40.1 weight percent water was mixed at 35 degrees centigrade for 5 hours. This solution was cast onto a non-woven polyester substrate then passed through a bath of 32 weight percent citric acid, 2 weight percent hydrochloric acid and 66 weight percent water and produced a filter with a mean clean water flow rate of 2.5 cc/min cm$^2$ at 27" mercury differential pressure and a bubble point of around 100 psi, a pore size of less than 0.1 um.

The heat exchanger and a different bath was then used to increase the pore size of the membrane produced from this solution batch. A solution at 39.5 degrees centigrade, and a bath of 22 weight percent citric acid, 1 weight percent hydrochloric acid and 77 weight percent water produced a membrane with a mean clean water flow rate of 37 cc/min cm$^2$ at 27" mercury differential pressure and a bubble point of 22-24 psi, indicating a pore size of approximately 0.5 um.

Scanning electron micrographs (SEMs) were taken of the resultant nylon 46 supported membrane.

Figure 2:
FIG. 2 is a scanning electron micrograph (SEM) taken at 500× magnification of a cross-section of a nylon 46 membrane prepared in accordance with Example 4 of the present invention.

FIG. 2 is a SEM taken at 500× magnification of a cross-section of the nylon 46 membrane. This SEM, which was taken at a slight angle, shows a face portion of the membrane at the lower right corner. The exterior portion of the membrane is very thin with small pores. Directly above the exterior portion of the membrane is an interior portion having larger interconnecting pores or chambers which do not appear at the exterior portion of the membrane. Directly above these larger interconnecting pores appears a void area comprising threads of the non-woven polyester substrate. At the upper left corner of FIG. 2 (above the void area), the larger interconnecting pores appear once again.

Figure 3:
FIG. 3 is a SEM taken at 498× magnification of an angled cross-section of a nylon 46 membrane prepared in accordance with Example 4 of the present invention.

FIG. 3 is a SEM taken at 498× magnification of an angled cross-section of the nylon 46 membrane. The face of the membrane with its small pores appears at the lower right corner of the SEM. Directly above the face portion is an interior portion of the membrane which has large interconnecting pores. Intertwined with the large interconnecting pores are threads of the non-woven polyester substrate.

Figure 4:
FIG. 4 is a SEM taken at 500× magnification of an angled cross-section of a nylon 46 membrane prepared in accordance with Example 4 of the present invention.

FIG. 4 is a SEM taken at 500× magnification of another angled cross-section of the nylon 46 membrane. This SEM more clearly defines the relationship between the face portion of the membrane with its small pores in the exposed surface and the interior portion which has large interconnecting pores which do not appear at the surface. As can be in this Figure, the surface includes discontinuities which do not extend into the interior portion of the membrane. Above the interior portion (at the upper portion of the SEM) is seen the void area comprising the threads of the non-woven polyester substrate.

The SEMs show the membranes of the present invention to have a unique internal structure. Each exterior surface of the membrane has fewer and smaller pores than the interior portion of the membrane. Beneath the exterior portion is a structure with much larger pores which are about five times the diameter of the largest pores in the exposed surface and which would offer less resistance to flow compared to the exterior portion. Because the exterior portion is very thin and the internal structure is very coarse, the rated pore size is achieved and the resistance to water flow is not increased for the membrane.

EXAMPLE 5

Clogging Resistance

An experiment was performed using ordinary tap water as the source of "dirty" fluid to determine clogging rates of nylon 46 filers versus commercially available nylon 66 filters. Samples of both nylon 46 and nylon 66 membranes were first tested for clean water flow rate and bubble point in order to identify membranes with similar pore size and flow rates. The nylon 46 membranes had a mean clean water flow rate of 16.5 cc/min cm2 at 27" mercury differential pressure while the nylon 66 membranes had a mean clean water flow rate of 19.8 cc/min cm2 at the same pressure. The bubble points of the nylon 46 membranes were 40, 42 and 44 psi while the bubble points of the nylon 66 membrane were 43, 45 and 46; both membranes sets having pore sizes of approximately 0.3 um.

Other 9.8 cm² disk samples of these membranes were then subjected to 50 ml of unfiltered tap water at a differential pressure of 27" mercury. For each 50 milliliter aliquot the time required to filter the fluid was recorded. Table 1 shows the sample of material tested, the filtration time (in seconds) for 50 ml of tap water, and the number of 50 ml aliquots filtered by the membrane sample. The tests were concluded when the filtration times increased approximately tenfold, an indication of filter clogging.

TABLE 1

| | | | | | | | | | | |
|---|---|---|---|---|---|---|---|---|---|---|
| Sample 1 Nylon 66 | | | | | | | | | | |
| 50 ml aliquot time (sec) | | | 16.8 | 41.2 | 96.0 | 158 | | | | |
| Sample 2 Nylon 66 | | | | | | | | | | |
| 50 ml aliquot time (sec) | | 16.3 | 27 | 59 | 92 | 149 | | | | |
| Sample 3 Nylon 46 | | | | | | | | | | |
| 50 ml aliquot time (sec) | 28 | 30 | 37 | 43 | 48 | 55 | 62 | 67 | 75 | 85 | 96 |
| Sample 4 Nylon 46 | | | | | | | | | | |
| 50 ml aliquot time (sec) | 25 | 32 | 41 | 48 | 57 | 63 | 70 | 77 | 85 | 92 | 100 |

For equivalent pore size material samples, flow rate decay, that is the time for filtration of each subsequent 50 ml portion of fluid, was found to be suprisingly lower for nylon 46 than nylon 66. A much larger volume of water was filtered by the nylon 46 representing a significant improvement in throughput ability of nylon 46 membranes and an increased resistance to clogging. In these samples throughput before clogging for the nylon 46 filters is more than double that of the commercially available nylon 66 filters.

A second experiment was performed to determine if the nylon 46 simply allowed more "dirt" to pass through without trapping it on the membrane. This experiment was carried out by filtering portions of 50 ml each, as above, of "dirty" fluid (tap water) through a nylon 46 membrane and using the filtrate, or collected, filtered water as the source of water for a nylon 66 membrane. (See Table 2)

TABLE 2

| | | | | | | | | | | |
|---|---|---|---|---|---|---|---|---|---|---|
| Sample 1 nylon 46 Unfiltered tap water | | | | | | | | | | |
| 50 ml aliquot time (secs) | 25 | 32 | 41 | 48 | 57 | 53 | 70 | 77 | 85 | 92 | 100 |
| Sample 2 nylon 66 Water pre filtered through sample 1 above | | | | | | | | | | |
| 50 ml aliquot time (secs) | | | 14 | | 14 | | 14 | | 14 | | 14 |
| Sample 3 nylon 66 Unfiltered tap water | | | | | | | | | | |
| 50 ml aliquot time (secs) | | | 16.5 | | 30 | | 90 | | 170 | | |
| Sample 4 nylon 46 Water pre filtered through sample 3 above | | | | | | | | | | |
| 50 ml aliquot time (secs) | | | 19 | | 19 | | 19 | | 19 | | |

As can be seen from the data, the nylon 66 membrane did not show any decay in flow time when the filtrate from a nylon 46 membrane was used in the flow decay test. This shows that the nylon 46 did retain the particles of dirt which would have clogged the nylon 66 membrane had the fluid not been pre filtered. Using the filtrate from a nylon 66 membrane in the flow decay test for a nylon 46 membrane (Samples 3 and 4) no flow decay was observed. Since neither type of membrane clogged when using the filtrate from the other, this data shows that the two membranes performed equally well in removing particles from tap water. However, it is clear that nylon 46 membranes have significantly higher throughput before clogging than nylon 66 membranes of comparable particle retention and pore size distribution.

EXAMPLE 6

Wettability

An experiment was performed to determine the wettability of nylon 46 membranes compared to nylon 66 membranes. Five sample filters, three of nylon 66 and two of nylon 46, were placed on the surface of various concentrations aqueous sodium chloride having surface tensions higher than pure water. Since increased surface tension reduces wettability of membranes, the time required for a 47 mm disk of membrane to completely wet out is indicative of filter wettability. The NaCl solutions provided a range of wet out times such that a wettability comparison of the sample membranes could be drawn.

TABLE 3

| WT. % NaCl | SURFACE TENSION dynes/cm | NYLON 66 0.6 um | NYLON 66 0.1 um | NYLON 66 1.2 um | NYLON 46 0.4 um | NYLON 46 0.2 um |
|---|---|---|---|---|---|---|
| 10 | 75.90 | instant | instant | instant | instant | instant |
| 15 | 77.68 | 2.3 secs | 2.5 secs | 2.5 secs | instant | instant |
| 25 | 82.12 | no wet* | no wet* | 24 secs | 0.5 secs | 0.4 sec |

*Filters did not wet out after 3 minutes

From Table 3 it can be seen that the nylon 46 membranes wet out in less time than nylon 66 membranes under conditions of higher surface tension. This demonstrates the advantage of nylon 46 over nylon 66 in wettability with fluids of higher surface tension, such as saline solutions.

The examples provided above are not meant to be exclusive. Many other variations of the present invention would be obvious to those skilled in the art, and are contemplated to be within the scope of the appended claims. For example, it is contemplated herein that blends incorporating minor amounts of nylons other than nylon 46 could be included to make materials having similar properties.

What is claimed is:

1. A porous material comprised of:
   (a) porous nylon 46;
   (b) whose pores have an average diameter of about 0.01 to 100 um as measured by bubble point or particulate challenge;
   (c) which is configured as a membrane; having a plurality of pores and an interior comprising large interconnecting pores that do not appear at said exterior surface, said large interconnecting pores being from about 2 to about 10 times larger than the largest pores located in said exterior surface;
   (d) having a fabric substrate supporting the membrane;
   (e) which substantially maintains its original wet out time after heating to a temperature necessary to seal two or more adjacent surfaces.

2. A porous material comprised of:
   (a) porous nylon 46;
   (b) whose pores have an average diameter of about 0.1 to 20 um as measured by bubble point;
   (c) which is configured as a membrane having a plurality of pores and an interior comprising large interconnecting pores that do not appear at said exterior surface, said large interconnecting pores being from about 2 to about 10 times larger than the largest pores located in said exterior surface;
   (d) having a fabric substrate supporting the membrane;
   (e) which substantially maintains its original wet out time after heating to about thermoplasticity.

3. A porous material comprised of:
   (a) porous nylon 46;
   (b) whose pores have an average diameter of about 0.1 to 20 um as measured by bubble point;
   (c) which is configured as a membrane having a plurality of pores and an interior comprising large interconnecting pores that do not appear at said exterior surface, said large interconnecting pores being from about 2 to about 10 times larger than the largest pores located in said exterior surface;
   (d) having a fabric substrate supporting the membrane;
   (e) which substantially maintains its original wet out time after steam sterilization.

4. A process for producing a porous material which substantially maintains its original wet cut time after heating to a temperature necessary to seal adjacent surfaces of the material, comprised of:
   (a) preparing a mixture of (i) one or more nylon 46 solvents selected from the group comprised of aqueous bronsted acids and (ii) one or more nylon 46 nonsolvents selected from the group comprised of alcohols and polar organic compounds;
   (b) dissolving nylon 46 into said mixture to form a solution;
   (c) precipitating a portion of the nylon 46 from the solution;
   (d) removing the nylon 46 nonsolvents from the precipitates to produce a microporous nylon 46 membrane having an exterior surface having a plurality of pores and an interior portion comprising large interconnecting pores, that do not appear at the exterior surface, said large interconnecting pores being from about 2 to about 10 times larger than the largest pores located on said exterior surface.

5. The process in claim 4, wherein:
   said nylon 46 solvents are selected from the group of aqueous bronsted acids comprised of hydrochloric acid, formic acid, phosphoric acid and/or mixtures thereof.

6. The process in claim 4, wherein:
   said nylon 46 nonsolvent alcohols and polar organic compounds are selected from the group comprised of water, aqueous citric acid, methanol, ethanol, propanol and/or mixtures thereof.

7. The process in claim 4, wherein:
   said solution contains 5–70 weight percent nylon 46 reagent concentrations solvents, 14–84 weight percent nylon 46 reagent concentration nonsolvents and 11–16 weight percent nylon 46.

8. The process in claim 4, wherein:
   said solution contains 5–70 weight percent nylon 46 reagent concentration solvents selected from the group of aqueous bronsted acids comprising of hydrochloric acid, formic acid phosphoric acid and/or mixtures thereof, 14-84 weight percent nylon 46 reagent concentration nonsolvent alcohols and polar organic compounds selected from the group comprised of water, aqueous citric acid, methanol, ethanol, propanol and/or mixtures thereof and 11-16 weight percent nylon 46.

9. The process in claim 4, wherein:
the nylon 46 is dissolved by blending at a temperature and for a period which does not degrade the polymer.

10. The process in claim 4, wherein:
the nylon 46 is dissolved into the nylon 46 solvent and nylon 46 nonsolvent mixture at a temperature range from about 25 to 75 degrees centigrade.

11. The process in claim 4, wherein:
the nylon 46 is dissolved into the nylon 46 solvent and nylon 46 nonsolvent mixture by blending.

12. The process in claim 4, wherein:
the nylon 46 is dissolved into the nylon 46 solvents and nylon 46 nonsolvent mixture at a temperature range from about 25 to 75 degrees centigrade while blending.

13. The process in claim 4, wherein:
precipitation of the nylon 46 and removal of the nylon 46 nonsolvents from the solution is by contact with a solution of about 0-60 weight percent reagent concentration of citric acid, formic acid and/or mixtures thereof, about 0-30 weight percent reagent concentration of hydrochloric, phosphoric acid and/or mixtures thereof, and 30-100 weight percent of one or more nylon 46 reagent concentration nonsolvents selected from the group comprised of water, methanol, ethanol, propanol and/or mixtures thereof.

14. The process in claim 4, wherein:
the nylon 46 nonsolvents are removed from the precipitate by extraction with water.

15. The process in claim 4, further comprised of:
drying the precipitate with air heated in the range of 80-150 degrees centigrade.

16. The porous material produced according to any one of claims 4-6.

17. The process in claim 4, wherein:
the nylon 46 nonsolvents are removed from the precipitate by evaporation.

18. A process for producing porous material which substantially maintains its original wet out time after heating to a temperature necessary to seal adjacent surfaces of the material, comprised of:
(a) dissolving 11-16 weight percent nylon 46 into a mixture of 5-70 weight percent nylon 46 reagent concentration solvents selected from the group hydrochloric acid, formic acid, phosphoric acid and/or mixtures thereof, and 14-84 weight percent reagent concentration nonsolvents selected from the group water, aqueous citric acid, methanol, ethanol, propanol and/or mixtures thereof to form a solution;
(b) precipitating the nylon 46 from the solution by contact with a solution of about 0-60 weight percent reagent concentration of citric acid or formic acid, or mixtures thereof, about 0-30 weight percent reagent concentration hydrochloric, or phosphoric acids or mixtures thereof, and about 30-300 weight percent reagent concentration nonsolvents selected from the group water, methanol, ethanol, propanol and/or mixtures thereof;
(c) removing the nylon 46 nonsolvents from the precipitate by extraction with water;
(d) drying the precipitate with air heated in the range of 80-150 degrees centigrade to produce a microporous nylon 46 membrane having an exterior surface having a plurality of pores, and an interior portion comprising large interconnecting pores that do not appear at the exterior surface, said large interconnecting pores being from about 2 to about 10 times larger than the largest pores located on said exterior surface.

19. A process for producing filters, which substantially maintain their original wet out time after heating to a temperature necessary to seal adjacent surfaces of the material, comprised of:
(a) dissolving 11-16 weight percent nylon 46 into a mixture of 5-70 weight percent nylon 46 reagent concentration solvents selected from the group hydrochloric acid, formic acid, phosphoric acid and/or mixtures thereof, and 14-84 weight percent concentration nonsolvents selected from the group water, methanol, ethanol, propanol, aqueous citric acid and/or mixtures thereof, to form a solution;
(b) dispersing the solution onto a nonwoven substrate;
(c) precipitating the nylon 46 from the solution by contact with a solution of about 0-60 weight percent reagent concentration citric acid, formic acid or mixtures thereof, about 0-30 weight percent reagent concentration hydrochoric or phosphoric acids and/or mixtures thereof, and 30-100 weight percent reagent concentration nonsolvents selected from the group water, methanol, ethanol, propanol and/or mixtures thereof;
(d) removing the nylon 46 nonsolvents from the precipitate by extraction with water;
(e) drying the precipitate with air heated in the range of 80-150 degrees centigrade to produce a microporous nylon 46 membrane having an exterior surface having a plurality of pores, and an interior portion comprising large interconnecting pores that do not appear at the exterior surface, said large interconnecting pores being from about 2 to about 10 times larger than the largest pores located on said exterior surface.

20. A process for producing porous material which substantially maintains its original wet out time after heating to a temperature necessary to seal adjacent surfaces of the material, comprised of:
(a) dissolving 11-16 weight percent nylon 46 into a mixture of 5-70 weight percent nylon 46 reagent concentration solvents selected from the group hydrochloric acid, formic acid and phosphoric acid and/or mixtures thereof, and 14-84 weight percent reagent concentration nonsolvents selected from the group water, methanol, ethanol, propanol, aqueous citric acid and/or mixtures thereof to form a solution;
(b) dispensing the solution in a uniform depth onto a nonwoven cloth substrate;
(c) precipitation of the nylon 46 from the solution by contact with a solution of about 0-60 weight percent reagent concentration citric acid or formic acid or mixtures thereof, about 0-30 weight percent reagent concentration hydrochloric or phosphoric acids and/or mixtures thereof, and 30-100 weight percent nonsolvents selected from the group water, methanol, ethanol, propanol and/or mixtures thereof;

(d) removing the nylon 46 nonsolvents from the precipitate by extraction with water;

(e) drying the precipitate with air heated in the range of 80-150 degrees centigrade to produce a microporous nylon 46 membrane having an exterior surface having a plurality of pores, and an interior portion comprising large interconnecting pores that do not appear at the exterior surface, said large interconnecting pores being from about 2 to about 10 times larger than the largest pores located on said exterior surface.

21. A microporous membrane comprised of nylon 46, comprising:

an exterior portion having a plurality of pores, and an interior comprising large interconnecting pores that do not appear at said exterior surface, said large interconnecting pores being from about 2 to about 10 times larger than the largest pores located in said exterior portion.

22. The microporous membrane of claim 21, wherein said interior portion further comprises a supporting matrix.

23. The microporous membrane of claim 21, wherein said interior further comprises a nonwoven cloth web.

24. The microporous membrane of claim 21, which has a porosity greater than about 50 percent.

25. The microporous membrane of claim 21, wherein said large interconnecting pores are about 5 times larger than the largest pores located on said exterior surface.

* * * * *

UNITED STATES PATENT AND TRADEMARK OFFICE
CERTIFICATE OF CORRECTION

PATENT NO. : 5,215,662
DATED : June 1, 1993
INVENTOR(S) : Johnson et al.

It is certified that error appears in the above—identified patent and that said Letters Patent is hereby corrected as shown below:

Column 11, lines 56-58:

Claim 1, line 14: Strike section (e) and replace it with the following:

--(e) having properties which enable it to substantially maintain its original wet out time after heating to a temperature necessary to seal two or more adjacent surfaces.--

Column 12, lines 3 and 4:

Claim 2, line 13: Strike section (e) and replace it with the following:

--(e) having properties which enable it to substantially maintain its original wet out time after heating to about thermoplasticity.--

Column 12, lines 17 and 28:
Claim 3, line 13: Strike section (e) and replace it with the following:

--(e) having properties which enable it to substantially maintain its original wet out time after steam sterilization.--

UNITED STATES PATENT AND TRADEMARK OFFICE
CERTIFICATE OF CORRECTION

PATENT NO. :   5,215,662

DATED     :   June 1, 1993

INVENTOR(S) :   Johnson et al.

It is certified that error appears in the above—identified patent and that said Letters Patent is hereby corrected as shown below:

Column 12, lines 29-32:

Claim 4, line 1:  Strike lines 1-4 and replace them with the following:

--A process comprising: producing a porous material which has properties for enabling it to substantially maintain its original wet cut time after heating to a temperature necessary to seal adjacent surfaces of the material, by--

Column 13, line 43:

Claim 16, line 2: delete "4-6" and replace with --4-15 and 17-20--.

Claim 18, line 1:  Strike lines 1-4 and replace them with the following:

--A process comprising: producing porous material which has properties for enabling it to substantially maintain its original wet cut time after heating to a temperature necessary to seal adjacent surfaces of the material, by--

Column 14, lines 12-15:

Claim 19, line 1:  Strike lines 1-4 and replace them with

UNITED STATES PATENT AND TRADEMARK OFFICE
CERTIFICATE OF CORRECTION

PATENT NO. : 5,215,662

DATED : June 1, 1993

INVENTOR(S) : Johnson et al.

It is certified that error appears in the above—identified patent and that said Letters Patent is hereby corrected as shown below:

the following:

>   --A process comprising: producing filters which have properties for enabling it to substantially maintain its original wet cut time after heating to a temperature necessary to seal adjacent surfaces of the material, by--

Column 14, lines 47-50:

Claim 20, line 1: Strike lines 1-4 and replace them with the following:

>   --A process comprising: producing porous material which has properties for enabling it to substantially maintain its original wet cut time after heating to a temperature necessary to seal adjacent surfaces of the material, by--

UNITED STATES PATENT AND TRADEMARK OFFICE
CERTIFICATE OF CORRECTION

PATENT NO.   : 5,215,662
DATED        : June 1, 1993
INVENTOR(S)  : Johnson et al It is certified that error appears in the above-indentified patent and that said Letters Patent is hereby corrected as shown below:

Column 16, line 5:

Claim 21, after "portion" add the following:

--; wherein said membrane has properties which enable it to substantially maintain its original wet out time after heating to a temperature up to thermal plasticity--

Signed and Sealed this

Third Day of May, 1994

Attest:

BRUCE LEHMAN

Attesting Officer        Commissioner of Patents and Trademarks